United States Patent
Rapaka et al.

(10) Patent No.: US 10,825,167 B2
(45) Date of Patent: Nov. 3, 2020

(54) RAPID ASSESSMENT AND OUTCOME ANALYSIS FOR MEDICAL PATIENTS

(71) Applicant: Siemens Healthcare GmbH, Erlangen (DE)

(72) Inventors: Saikiran Rapaka, Pennington, NJ (US); Lucian Mihai Itu, Brasov (RO); Tiziano Passerini, Plainsboro, NJ (US); Puneet Sharma, Monmouth Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 343 days.

(21) Appl. No.: 15/499,934

(22) Filed: Apr. 28, 2017

(65) Prior Publication Data

US 2018/0315182 A1    Nov. 1, 2018

(51) Int. Cl.
*G06N 5/04* (2006.01)
*G06T 7/00* (2017.01)
(Continued)

(52) U.S. Cl.
CPC .......... *G06T 7/0012* (2013.01); *G06K 9/6257* (2013.01); *G06N 5/04* (2013.01);
(Continued)

(58) Field of Classification Search
CPC .......... G06N 20/00; G06N 3/08; G06N 7/005; G06N 3/0472; G06N 3/0454; G06N 3/084;
(Continued)

(56) References Cited

U.S. PATENT DOCUMENTS 7,244,230 B2 * 7/2007 Duggirala ................ A61B 8/00
                                                      600/300
7,650,321 B2 * 1/2010 Krishnan ................ G16H 10/60
                                                       706/60
(Continued)

FOREIGN PATENT DOCUMENTS

CN     104115150 A     10/2014
CN     105163657 A     12/2015
(Continued)

OTHER PUBLICATIONS

Zhang et al., Learning Classifiers from Synthetic Data Using a Multichannel Autoencoder, Mar. 11, 2015 [retrieved Jul. 1, 2019], Computer Vision and Pattern Recognition:Machine Learning: arXiv:1503.03163v1,pp. 1-11. Retrieved: https://arxiv.org/abs/1503.03163v1 (Year: 2015).*

(Continued)

*Primary Examiner* — Andrew M Moyer
*Assistant Examiner* — Dennis Rosario (57) ABSTRACT

Machine learning is used to assess data for a patient in an emergency, providing rapid diagnosis based on a large amount of information. Assistance in triage may be provided. Given the large variety of patients and conditions that may occur, the machine learning may rely on synthetically generated images for more accurate prediction. The machine learning may accurately predict even with missing information and may be used to determine what missing information for a given patient is more or less important to obtain.

16 Claims, 3 Drawing Sheets

(51) Int. Cl.

| | | |
|---|---|---|
| *G16H 50/20* | (2018.01) | |
| *G06N 20/00* | (2019.01) | |
| *G06K 9/62* | (2006.01) | |
| *G16H 30/40* | (2018.01) | |
| *G16H 50/70* | (2018.01) | |
| *G16H 40/20* | (2018.01) | |
| *G16H 50/30* | (2018.01) | |
| *G06N 20/20* | (2019.01) | |
| *G06N 7/00* | (2006.01) | |
| *G06N 3/04* | (2006.01) | |
| *G06N 5/02* | (2006.01) | |
| *G06N 20/10* | (2019.01) | |
| *G06N 5/00* | (2006.01) | |

(52) U.S. Cl.
CPC .............. *G06N 20/00* (2019.01); *G06N 20/20* (2019.01); *G16H 30/40* (2018.01); *G16H 40/20* (2018.01); *G16H 50/20* (2018.01); *G16H 50/30* (2018.01); *G16H 50/70* (2018.01); *G06K 2209/05* (2013.01); *G06N 3/0454* (2013.01); *G06N 5/003* (2013.01); *G06N 5/025* (2013.01); *G06N 7/005* (2013.01); *G06N 20/10* (2019.01); *G06T 2207/10081* (2013.01); *G06T 2207/20081* (2013.01); *G06T 2207/20084* (2013.01); *G06T 2207/30048* (2013.01)

(58) Field of Classification Search
CPC .......... G06N 20/20; G06N 5/02; G06N 3/088; G06N 5/045; G06N 5/046; G06N 5/04; G06T 2207/20081; G06T 7/0012; G06T 2207/20084; G06K 9/6256; G06K 9/6267; G06K 2209/05; G16H 50/20; G16H 10/60; G16H 15/00; G16H 50/50; G16H 50/30; G16H 50/70; A61B 5/7267; A61B 5/7275; A61B 5/7264; G06Q 10/06; G06Q 10/063; G06Q 10/06311; G06Q 50/24; G06Q 10/0635; G06F 17/18; G06F 16/35; G06F 16/285
See application file for complete search history.

(56) References Cited

U.S. PATENT DOCUMENTS

| | | | |
|---|---|---|---|
| 7,744,540 B2 | 6/2010 | Rao et al. | |
| 8,060,178 B2* | 11/2011 | Zhou | G16H 50/20 |
| | | | 600/407 |
| 8,343,053 B2* | 1/2013 | Feng | G06T 7/73 |
| | | | 600/443 |
| 9,717,417 B2* | 8/2017 | DiMaio | A61B 5/0075 |
| 10,152,761 B2* | 12/2018 | Kress | G06Q 30/0631 |
| 10,213,622 B2* | 2/2019 | Bharat | A61N 5/1039 |
| 10,468,136 B2* | 11/2019 | Tekumalla | G06N 20/00 |
| 10,529,445 B2* | 1/2020 | Cossler | G06F 19/00 |
| 2014/0365232 A1* | 12/2014 | Sadeghi | G16H 50/20 |
| | | | 705/2 |
| 2015/0025405 A1 | 1/2015 | Vairavan et al. | |
| 2015/0213217 A1 | 7/2015 | Amarasingham et al. | |
| 2016/0027342 A1 | 1/2016 | Ben-Haim | |
| 2016/0148371 A1 | 5/2016 | Itu et al. | |
| 2016/0328525 A1 | 11/2016 | Gross et al. | |
| 2017/0032090 A1 | 2/2017 | Kamen et al. | |
| 2017/0039344 A1* | 2/2017 | Bitran | G06F 19/3475 |

FOREIGN PATENT DOCUMENTS

| | | |
|---|---|---|
| CN | 105765584 A | 7/2016 |
| WO | WO2016075331 A2 | 5/2016 |

OTHER PUBLICATIONS

Song et al., Eyes closeness detection from still images with multi-scale histograms of principal oriented gradients, Sep. 2014 [ retrieved Jul. 1, 2019], Pattern Recognition, vol. 47, Issue 9,pp. 2825-2838. Retrieved: https://www.sciencedirect.com/science/article/pii/S0031320314001228 (Year: 2014).*

Miller et al., Learning from one example through shared densities on transforms, Jun. 15, 2000 [retrieved Jul. 1, 2019], Proceedings : IEEE Conf Computer Vision Pattern Recognition, 8 total pages. (Year: 2000).*

Viola et al., Alignment by Maximization of Mutual Information, Sep. 1997 [retrieved Jul. 1, 2019], International Journal of Computer Vision, vol. 24, Issue 2,pp. 137-154. Retrieved: https://rd.springer.com/article/10.1023/A:1007958904918 (Year: 1997).*

Khan et al., A Hybrid Design for Medical Decision Support using Data Mining to Impute Missing Data, uploaded Feb. 3, 2015 [retrieved Mar. 14, 2020], 9 pgs. Retrieved: https://www.researchgate.net/publication/265109402_A_Hybrid_Design_for_Medical_Decision_Support_using_Data_Mining_to_Impute_Missing_Data (Year: 2015).*

Partial European Search Report dated Sep. 24, 2018 in corresponding European Patent Application No. 18168022.4.

Chinese Office Action dated Jul. 3, 2020 in corresponding Chinese Patent Application No. 201810409398.2.

\* cited by examiner

RAPID ASSESSMENT AND OUTCOME ANALYSIS FOR MEDICAL PATIENTS

BACKGROUND

The present embodiments relate to medical diagnosis and/or prognosis in emergency assessment of patients. Every year, millions of patients with a wide range of pathological conditions are inspected at emergency departments. For such patients, a multitude of data is commonly collected, including blood pressure measurements, ECG, past patient history, a summary of symptoms, and imaging data such as computed tomography (CT), ultrasound, or magnetic resonance imaging (MRI) images. The patient treatment is then decided based upon the information in this collection. The information needs to be processed as soon as possible, especially to identify patients in need of urgent medical intervention. This process is currently handled manually, placing a lot of stress on the emergency department. The analysis of this large collection of data may delay triage or treatment even in the emergency situation. Other tests may be prescribed after analysis by a physician, causing further delay and complicating the assignment of order in treatment among multiple patients.

SUMMARY

By way of introduction, the preferred embodiments described below include methods, computer readable media and systems for assessment and/or outcome determination in a medical system. Machine learning is used to assess data for a patient in an emergency, providing rapid diagnosis based on a large amount of information. Assistance in triage may be provided. Given the large variety of patients and conditions that may occur, the machine learning may rely on synthetically generated images for more accurate prediction. The machine learning may accurately predict even with missing information and may be used to determine what missing information for a given patient is more or less important to obtain.

In a first aspect, a method is provided for assessment and/or outcome determination in a medical system. Medical scan data representing anatomical structures of patients being triaged in an emergency department of a hospital is acquired. Other data for the patients is obtained. A set of features are extracted from the medical scan data and the other data. A processor inputs the features to a machine-trained classifier. The machine trained classifier is trained, at least in part, from synthetically generated images not specific to training data for existing patient cases. The processor determines, with application of the machine-trained classifier to the features, conditions of the patients and risks for the conditions. An order for triage of the patients is provided based on the risks. A missing source of information is output based on the features that are available for a first of the patients and the condition for the first patient.

In a second aspect, a method is provided for assessment and/or outcome determination in a medical system. Medical scan data representing anatomical structures of a patient in an emergency is acquired. Other data for the patient is obtained. A set of features are extracted from the medical scan data and the other data. The processor determined, with application of the machine-trained classifier to the features, a condition of the patient, a risk for the patient, an outcome for the patient, a similar patient, or combinations thereof. A missing source of information is output. The missing source is based on missing features for the patient.

In a third aspect, a method is provided for machine-training to assess or determine outcome for a patient. Parameters of an anatomical model are varied. The variation provides a set of anatomical models generated synthetically. Medical images are emulated from the synthetically generated anatomical models of the set. A machine trains a machine-learnt classifier using the emulated medical images.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The collection of data from the patient images and measurements presents a very complex network of information about the patient. This complex network of information may be effectively untangled by modern machine learning algorithms. A machine-learnt classifier provides fast patient assessment and outcome analysis. Modern machine learning and artificial intelligence algorithms are well suited to managing large quantities of heterogeneous data. Consistent predictions are provided in an automated manner. Machine learning algorithms have superior predictive capabilities in complex tasks, showing expert-level performance. A comprehensive patient assessment model combines all available information from the patient to present an integrated understanding of the patient state as well as enable the clinician to guide therapy.

Using heterogeneous data sources, the machine-learnt classifier automatically classifies the patient population and highlights additional sources of information, which if collected may add the most additional information to better diagnose or treat the patient. In particular, the system evaluates the existing sources of data to make a model prediction of the risk of presence of different pathological conditions. In addition, the model computes the likely probabilities of these different conditions and automatically flags high-risk patients who need priority evaluation from clinical providers.

One example application is in emergency scenarios, such as where a patient presents with a chest pain in an emergency room. Under such conditions, based on patient history, the patient might be given some kind of an imaging exam such as a CT, MRI, ultrasound, or stress test. There are multiple likely sources of the chest pain, including coronary obstruction, aortic dissection or a problem with the pulmonary arteries. Under such conditions, it is important to identify that subset of patients with life-threatening conditions who may suffer adverse outcomes due to any delay. The machine-learnt model uses the imaging tests, patient blood biomarkers, non-invasive measurements (e.g., blood pressure and heart rate), and/or other available information to quickly perform a triple rule-out, to identify the likely source of chest pain along with a risk associated with the condition.

In scenarios where the available information leads to an uncertain prediction due to missing information, the model may consider further sources of information (such as other kinds of imaging including stress tests and perfusion imaging, or blood tests for additional biomarkers) to suggest or rank the sources of missing information in order of highest information gained. For each of the different conditions, the model may also evaluate quantitative markers that estimate the degree of severity of the condition. For instance, when it is determined that the coronary arteries have a severe occlusion, the model may automatically calculate markers such as Fractional Flow Reserve and related hemodynamic indices.

Figure 1:
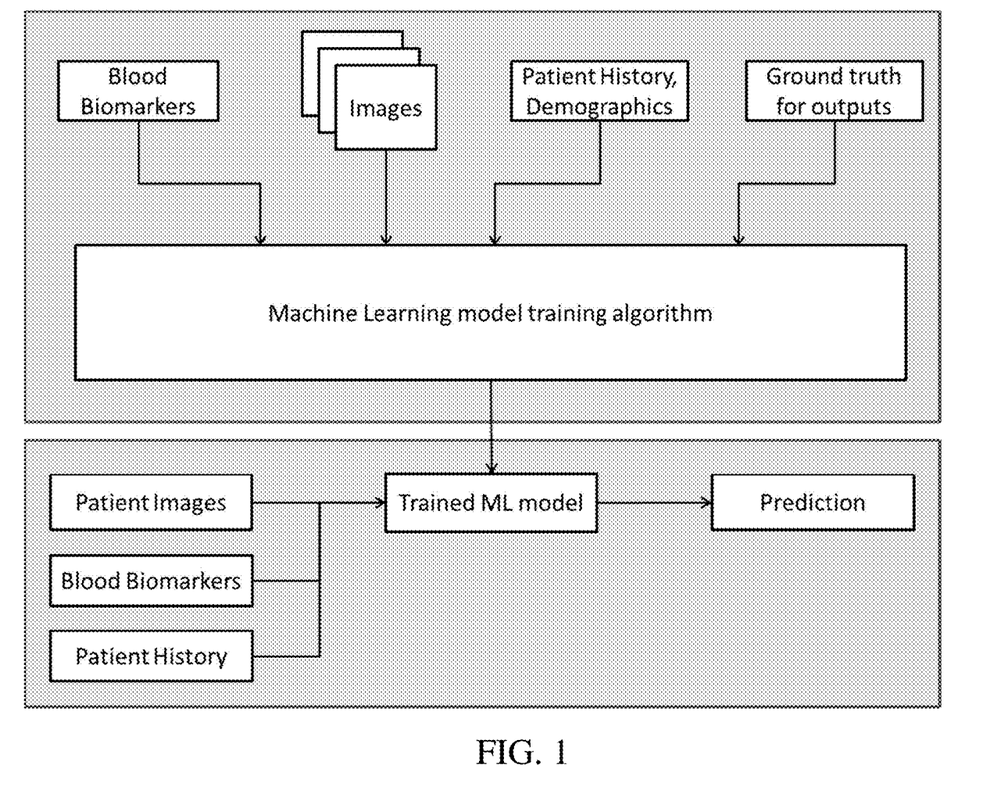
FIG. 1 is a medical system representing both training and application of a machine-learnt classifier for use in emergencies.

Machine learning has two main phases: a training phase and an application or testing phase. During the training phase, the model is trained using heterogeneous data. During the testing or application phase, the model is then applied to patient data to make predictions. FIG. 1 shows an example schematic description of the model training and testing phases. The top box represents the training phase using multiple data sources to produce the trained model. In the testing phase of the bottom box, the model is applied on patient data to make a prediction.

In both phases, features are extracted from the data. The features are then used to train and/or apply the trained classifier. Various examples herein may be for the training phase or the testing phase. The same examples may be used in the other of the phases.

Figure 2:
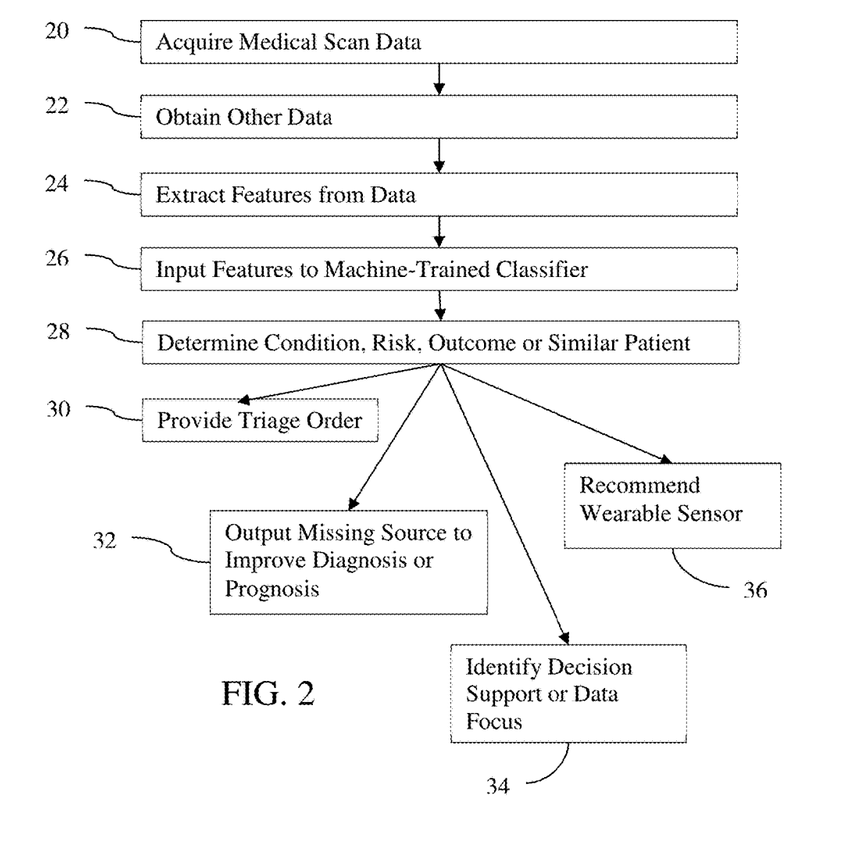
FIG. 2 is a flow chart of one embodiment of a method for assessment and/or outcome analysis in a medical system.

FIG. 2 is a flow chart diagram of one embodiment of a method for assessment and/or outcome determination in a medical system. The method relates to application of a machine-trained classifier for rapid results. The machine-trained classifier is trained to diagnose and/or make a prognosis for one or more patients in an emergency situation. Data available in typical emergency situations is used to train the classifier to automatically assess in a rapid manner, assisting physicians in their diagnosis or prognosis.

Figure 6:
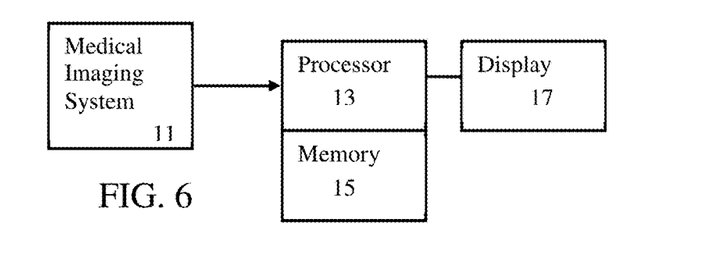
FIG. 6 is a block diagram of one embodiment of a medical system for assessment and/or outcome determination.

The medical system of FIG. 6 or other medical system implements the acts. The system may be a medical imaging system, a hospital workstation, a patient medical records computer, a medical server, or other secure medical data processing system. The medical system may or may not include a memory or database, such as patient medical record database and/or picture archiving and communications system (PACS).

The acts of FIG. 2 are performed in the order shown (numerical or top to bottom) or other orders. For example, acts 20 and 22 occur simultaneously or in any order. As another example, acts 30-36 may be performed in any order.

Additional, different, or fewer acts may be provided. For example, any of acts 30-36 may or may not be performed. As another example, one of acts 20 or 22 is not performed. Example additional acts include input of features to other machine-learnt classifiers and/or other uses of machine-learnt classification.

In act 20, the medical system acquires medical scan data. The medical scan data is acquired by loading from memory. Alternatively or additionally, the medical scan data is acquired by a medical imaging system, such as an x-ray, CT, MRI, ultrasound, camera, or other scanner. The medical imaging system is part of or is the medical system, or the medical system acquires the scan data by transfer from the imaging system over a computer network.

The medical scan data represents a one, two, or three-dimensional region of the patient. For example in 3-D imaging using any of different modalities, a set of scan data representing intensity at different voxels distributed over three dimensions is acquired. In other embodiments, the medical scan data is two-dimensional representation of a plane or projection through the patient.

The medical scan data represents anatomical structures of the patient or patients. Any anatomy may be represented, such as part of the cardiac system (e.g., CT scan of the heart and surrounding or connected vessels).

The medical scan data represents a patient in an emergency situation. For example, the medical scan data is acquired due to a patient's visit to an emergency room and/or by an EMT in an ambulance or while visiting a patient. The medical scan is acquired to assist in diagnosing the condition of the patient. In alternative or additional embodiments, the medical scan data is acquired during a routine visit or in a non-emergency.

The medical system may acquire scan data from a past scan of the patient. The different data used for training the model or application for a given patient may either be acquired at the same time or at different times. For example, past medical information and medical images of the patient are used in combination with the current medical information to get a comprehensive picture of the patient condition as well as how the condition has evolved. Such information may be sampled in the training database, either by using patient information from the hospital databases at different instant of times, or by using mathematical models of disease progression (e.g., model of plaque growth), along with the information at a given time, or a combination of these approaches.

The medical scan data is acquired for a given patient. For triage in an emergency department of a hospital, the medical scan data for multiple patients is acquired. Each patient is to be diagnosed in order to determine the highest risk condition. The patients with higher risk may be treated first, so the machine-trained classifier learns to assess the medical scan data of the patients in order to determine the relative risk level. The determination may be by patient. Alternatively, the classifier determines relative risk as an output given features from many patients in application.

In act 22, the medical system obtains other data for the patients. The data is obtained by access to a memory, loading from memory, or transfer through an interface device. The other data is in one or more memories and/or from one or more sensors. The data is obtained from a computerized medical record, billing database, department records, picture archiving and communications system (PACS), or another source. A textual clinical report for the patient may be mined.

Models may be trained or applied using a multitude of different sources of data. Hospital medical records along with any available patient outcome data are mined for training. The medical records may be mined for application for a patient in the testing phase. The machine learning algorithms use such information as the text in the clinical reports, medical images, blood biomarker information, patient demographics (e.g., age, race, gender, weight, BMI, or others), patient history (e.g., smoking, alcohol consumption, high blood pressure, drug use, current medicines being used, or others), non-invasive measurements (e.g., blood pressure, heart rate, ECG signals, or others), and/or information from other devices and sensors. The models may also use genomic information from the patient. For example, the presence of specific genomic markers is used to evaluate either the probability of currently experiencing or the predisposition to develop any pathological conditions. The model may use the results of physiological modeling using patient data as input (e.g. blood flow, electrophysiology, biomechanics quantities, or others).

The data is from a past examination of the patient (e.g., previous image, demographics, and patient history) and/or includes current information. For example, a previous examination provides some of the information. Symptoms being currently experienced are also obtained. Other current measurements, such as CT imaging and blood biomarkers, are obtained. Obtaining the same type of data from different times may show progression. Disease progression can also be inferred by looking at past patients with closely matching disease characteristics and their outcomes.

In act 24, the medical system extracts a set of features from the medical scan data and/or the other data. The feature extraction is performed on a medical imaging scanner or on another device, such as an imaging workstation. A processor performs the extraction with or without user input through a user interface. Requests, mining, or searching formatted for the source obtains the data.

The process of feature extraction from images is fully automated, semi-automated, manual, or a combination of thereof. Under a manual approach, anatomical or other features are input, annotated, or measured by a human operator or user. For example, an imaging scanner or workstation displays a dialog that the user can edit to insert the features. The image is used to determine the values for the features. As another example, the user traces on an image. The resulting list of values for the features is stored as part of the training database or is used for application of the machine-learnt classifier.

Under an automated extraction, the medical system calculates values for the features. Segmentation, thresholding, filtering, template matching, detection (e.g., machine learnt detection), other image processing, or combinations thereof are used to extract values specific to anatomy represented in the image. Alternatively or additionally, Haar wavelets, steerable features, the intensity values without processing, or other features calculated across the image regardless of represented anatomy are used.

Within the medical image, the model may use multiple features. For a cardiac example, total scar burden, perfusion information, calcium scoring, plaque quantification, aggregate plaque volume, size and location of plaque, and/or the morphology of plaque (e.g., soft or calcified) is determined by image processing. The model may utilize advanced radio-genomic phenotype information inferred from the image. For example, a tumor is detected. The texture of the tumor may indicate the genetic make-up of the patient. Patients with different genes have different types or textures of tumors. Other image indicated phenotype information may be extracted. In other embodiments, the phenotype is extracted from a genetic report or analysis.

A machine-learnt detector or classifier may be used to extract. In one implementation, quantitative features are extracted from the image, such as Haar wavelet features. These features are then used to train a machine learning model. Once the model is trained, a similar set of features is also computed for new patients and then fed as input to the model. The model then produces the required outputs as extracted features from the image. One machine-learnt classifier is trained to extract features input to another machine-learnt classifier trained to output condition, providing a cascade of two or more machine-learnt or trained classifiers. The models may use a combination of a wide range of learning algorithms in a cascaded manner. The cascade may be used for imaging and/or the other data. For example, the text in the clinical reports is processed using machine-learnt natural language processing tools to identify the key information content. As another example, medical images are processed by any machine learning models including deep convolutional neural networks, kernel based methods, or others. The information and features extracted from these different sources is then aggregated to train a complex higher-order model or machine-learnt classifier, which predicts the patient condition, outcome, and/or risk score.

In acts 26 and 28, the medical system applies one or more machine-learnt classifiers. The input of the extracted features from act 24 in act 26 results in the output for act 28. A processor inputs the features, applying the machine-learnt classifier to the input features to determine the condition, risk, outcome, and/or identification of similar patient or patients.

The condition may be a diagnosis, such as a cause of the emergency. For a cardiac example, the condition is one of coronary obstruction, aortic dissection, or a problem with the pulmonary arteries. The risk may be for any time frame. For example, the risk of further harm (e.g., worsening condition) to the patient over the next number of minutes, hours, days, weeks, months, and/or years due to the condition is predicted. The risk may be known based on the condition. The outcome is a prediction of results of a given treatment and/or due to a condition. The outcome may be a length of occurrence of the condition without treatment, a life expectancy with and/or without treatment, reoccurrence, or other information depending of various treatment options. Identification of similar patients may be based on any measure of similarity between any aspect (e.g., condition, severity of condition, location, size, or other information). The identification may be distributed, such as similar patients treated in different ways or with different outcomes.

For training, the extracted features and known ground truth (i.e., condition, risk, outcome, and/or identification of similar patient or patients) for the samples of the training data are used to learn to classify. The input feature vectors and corresponding results for many samples are used in machine learning. Tens, hundreds, or thousands of examples are used to train. The corresponding feature values are used to map the feature values to the results.

One classifier may be trained to predict multiple types of results. For example, the same classifier predicts two or more of the condition, risk, outcome, or identification of similar patients. The classifier may predict the condition with or without severity and then look-up is used to determine the risk. Alternatively, different classifiers are used for different types of results, such as one classifier indicating a condition and another classifier in a cascade indicating the risk and/or outcome.

In an emergency environment, many different conditions may be possible. As a result, one or more classifiers may be used to determine a category of conditions for a patient and other classifiers are used to determine specific conditions given the category. A decision tree, cascade, or other hierarchy of classifiers may be used as the machine-learnt classifier. In alternative embodiments, the user selects the classifier to be used based on initial symptoms or determination (e.g., selecting a cardiac classifier where the patient shows signs of chest pain).

Rather than training one classifier, the classifier may be learned as a network of different models, where each model works on some subset or the entirety of the feature space. The outputs from each model may be used as inputs to other models, thereby creating new features. The output from one model may be used as an input to the same model to produce recursive model estimates. The classifier may be trained to learn from categorical, discrete, and/or continuous features. The predictive classifier may be a combination of multiple interacting machine-learnt classifiers, each of which use the same or a different subset of features. The outputs from one model can be used as an input to another classifier.

In one embodiment, the machine-learnt model is implemented as a multi-task neural network. Such networks have a pool of shared layers to determine common features to the task at hand and additional layers that are trained for specific tasks. Alternatively, an entire network is shared, and additional networks are coupled in a cascaded manner to learn the specific tasks. For example, the multi-task problem is formulated as processing the acquired images to generate quantitative information with a general task of image segmentation (regardless of the image modality and/or anatomy of interest) and with specific tasks of segmentation of specific anatomies and/or from specific imaging modalities. As another example to augment the input data with physiological modeling, the general task is computation of a functional index (e.g., fractional flow reserve), and the specific tasks are computing fractional flow reserve in the coronary circulation, an analogous index in the pulmonary circulation, and/or an analogous index in the aorta.

Any type of machine learning algorithm may be used. The machine learning is supervised, semi-supervised, or unsupervised. Some examples using supervised learning include regression, instance-based methods, regularization methods, decision tree learning, Bayesian, kernel methods, clustering methods, association rule learning, artificial neural networks, dimensionality reduction, and ensemble methods. Probabilistic boosting tree, hierarchal, or other processes may be used.

The machine learning may use all of the input features. Alternatively, the machine learning determines discriminative features and selects a feature set to be used for classifying. A subset of the extracted features may be used for learning, as determined from feature selection and ranking, feature combination, or other process.

Collecting a statistically significant number of training samples (e.g., thousands of patients with known results for a given condition or number of conditions) may be difficult. Some of the training data may be synthetically generated to fill any gaps or for the entirety of the training data. It may be difficult to locate many samples of patients suffering from one or more conditions, combination of conditions, or specifics to a condition (e.g., two blockages at a specific combination of amount and/or locations of blockage). Synthetic examples may be created. Rather than using specific existing patient cases for the training data, data not specific to an existing or previously handled patient is used. The machine-trained classifier is trained only from synthetic data or from a combination of data from a collection of patients and synthetic data.

Figure 3:
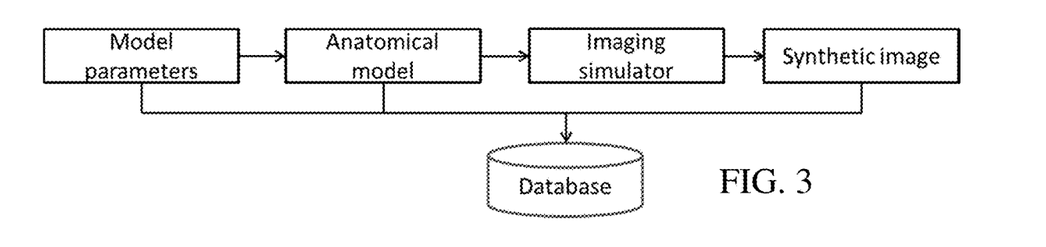
FIG. 3 illustrates creation of training data by simulation of imaging from variation in an anatomical model.

The synthetic data may be for the other data and/or the medical scan data. In one embodiment, the synthetic data is of medical images. The machine-trained classifier is trained from examples of images generated with computer modeling, physical modeling, or both computer and physical modeling using in vitro or in silico models and corresponding ground truths. FIG. 3 shows an example. An anatomical model is provided with different values of one or more parameters, resulting in different anatomical models. An image simulator then simulates generation of one or more images from each of the anatomical models. The resulting synthetic images are stored in a database. The values of the parameters, the anatomical models, and/or information derived there from (e.g., pathological condition being modeled) are stored in the database as the ground truth for the synthetic images.

Figure 4:
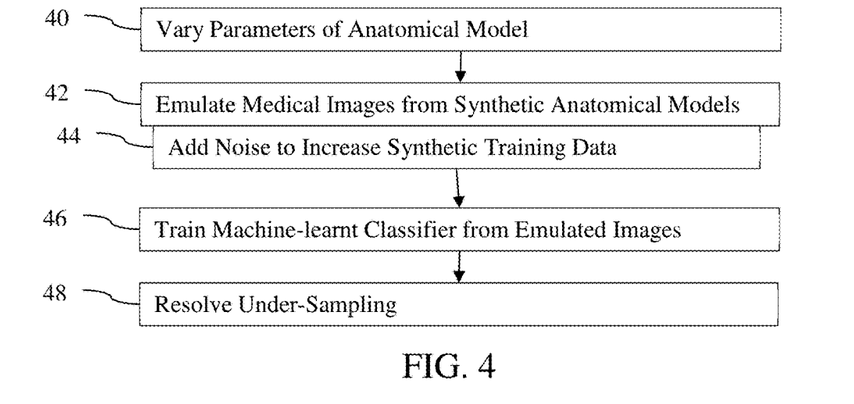
FIG. 4 is a flow chart diagram of one embodiment of a method for training from synthetically generated images.

FIG. 4 is a flow chart diagram of one embodiment of a method for machine training to assess or determine outcome for a patient using a database populated, at least in part, by synthetically generated images. The approach of using synthetic images and datasets has the advantage of being able to span pathological conditions that are relatively rare and hard to sample from the patient population in sufficient numbers. The large number of variations available is one benefit of using synthetic data for training.

The acts are performed in the order shown or a different order. For example, the process loops back from act 48 to act 40 to repeat the process to address under-sampling in the training database. Additional, different, or fewer acts may be used, such as not performing act 48 and/or act 44.

In act 40, the processor varies parameters of an anatomical model. Any anatomical model may be used, such as a computer-generated model, a model representing a statistical average across patients, a physical model (e.g., phantom or structure), a model from a study, and/or a model from a medical atlas. The anatomical model is defined by one or more parameters. For example, shape, diameter, volume, location of bifurcation, rate of change, curvature, cross-sectional area, or other parameters are provided. Parameters quantifying one or more conditions are provided as well.

A starting model may be created from a given patient, but the majority of training examples are based on alterations from the starting model. Alternatively, the starting model or models are averages or other models not directly related to a given patient. The data is synthetic by not being extracted from data for particular patients to represent that specific patient (i.e., the model is not specific to a patient). The digital representation is generated and stored on a computer. In alternative embodiments, some or a majority of the training examples are extracted from patient-specific data for a plurality of patients and only some of the examples are alterations of those models. If real patient anatomies are available, further synthetic models may be constructed by stochastically perturbing the features of the patient anatomy. This added synthetic data may be used to get a richer representation, which can account for uncertainties in the data.

To model any given condition, the values of the parameters are set. Other values may be provided for other parameters to produce further examples for a given condition. Other values of some parameters may be used to model different conditions. By varying the values, a set of anatomical models are generated synthetically. Additional examples for training are created by altering one or more values of variables for the anatomical structure and/or for generating the anatomical structure. Any number of different parameters may be varied. Hundreds or thousands of different examples for training may be generated from a single starting model.

The variation may be controlled or user set. Alternatively or additionally, the variation is random. For example, thousands of stochastic perturbations to the synthetic anatomical model produce thousands of corresponding anatomical models. Since the anatomical models have known conditions, a rich dataset on which to train the machine learning model is provided. The stochastic variation may be of parameters with a same condition. Alternatively, the stochastic variation samples across conditions.

To populate the database, different approaches may be used. One or more baseline models, whose properties are then randomly or systematically perturbed to obtain a large number of models, are created. In another approach, each model is generated separately by following a set of rules and by randomly or systematically perturbing the parameter values of these rules. Scaling laws may be used for generating realistic synthetic models.

The values of the parameters are either chosen randomly for each synthetic example (e.g., true or false for binary variables or a value in a predefined range for continuous variables) or the entire parameter space is explored systematically within limited ranges when generating the database of synthetic examples. Any type of distribution may be used for the continuous variables, such as uniform, normal, or other. Known, estimated, or standard normal distributions may be used. Other sources of variability may be used to create the synthetic examples for training.

In act 42, the processor emulates medical images from the synthetically generated anatomical models of the set. The various anatomical models are used to generate one or more images. By modeling the image forming process or the medical scanner, a synthetic image is generated from the synthetic anatomical model. For example, the image formation process of a CT scanner is applied to the anatomical model, resulting in a synthetic image simulating medical scanning of the anatomy. Any forward modeling to produce the synthetic image may be used.

In act 44, additional samples for training are created by altering the emulated images. The processor adds different degrees of statistical noise to each of the emulated medical images, resulting in a plurality of additional images for each of the emulated medical images. The result is additional synthetic images with known ground truth for training.

To increase robustness, different transformations may be applied to the training data to produce additional training samples. For instance, different degrees of statistical noise are applied to medical images (synthetic or actual) to produce additional synthetic medical images. The addition of the noise does not alter the ground truth, allowing for the machine training to learn to provide the same final prediction regardless of the noise level. Noise may be introduced into the anatomical model. Other variations in the image and/or model may be used, such as translation, scale, and/or rotation to produce additional images from a given sample.

In act 46, a machine trains the machine-learnt classifier using, at least in part, the emulated medical images. A processor performs the machine learning using the training data.

Using synthetic modeling instead of requiring examples from a large collection of patients for training data provides several advantages. A very large number of cases may be automatically generated, leading to an extensive database. Complex pathological configurations may be generated, such as serial stenoses, multi-branch stenoses, bifurcation stenoses, diffuse disease, or others, despite being rare among actual patients. Rare pathological cases may be sampled better. Since the generation of synthetic in silico geometries may be completely automated, the cost of generating a large database is reduced as compared to assembling patient examples. The examples may be extended to different demographic groups easily. The training may be done in a global manner or a site-specific manner, allowing the system to account for anatomical trends based on patient demographics and epidemiology. Finding sufficient examples in a local region may be difficult. The training may be iteratively improved with either more data or with better representations of the features.

Once the synthetic images have been generated, the features which are used for training the machine learning algorithm are extracted from the images. The same features or some subset of the features are extracted from the medical images of the patient in application and used for predicting the results using the trained model. Depending on the source and type of the input data, the extracted features may be binary, numerical, categorical, ordinal, binomial, interval, text-based, or combinations thereof.

Any type of features may be used. Morphological features may be used. The machine learning process may provide for certain features to be used and others not to be used. To train, the features to be used may be selected by a programmer. Some example features may include the parameters used or selected to define or create the anatomical model. Other or different features may additionally or alternatively be extracted.

In act 48, the trained classifier is checked for under-sampling. Since synthetic images are used for training, additional synthetic images may be created to re-train or update the training where the results output by the classifier are less accurate. To check, the processor applies the machine-learnt classifier to test data with known ground truth. The results are examined for accuracy. If predictions for a given category (e.g., condition) are not of a desired accuracy, then the training data may be under-sampled for that category. Additional samples are generated for the category and added to the training data. The machine-learnt classifier is re-learnt with the additional emulated medical images.

Returning to FIG. 2, the medical system determines the result in act 28. The extracted features for a particular patient are input in act 26.

In one embodiment, the machine-learnt classifier determines risk using a dictionary. The training data is clustered or compressed, providing dictionary reference information. Nearest neighbor matching, clustering, or other approaches may be used. The different datasets are used to create a dictionary of patient data, along with the corresponding clinical outcomes. When a new patient is presented to the system, the medical system finds a subset of the closest matches in the dictionary or database, and presents a summary of their outcomes to the user. This summary of outcomes indicates the risk for the patient.

Where one or more values for features are unknown for a given patient, then substitutes may be used for the values of the missing features. For example, values from patients with similar features are found. As another example, average or default substitutes are used. In one embodiment, the application is repeated for a distribution of different values for the missing feature or features, providing a range of results depending on the missing information.

For a given patient, the machine-learnt classifier determines the results from the input feature vector. For example, the condition and/or risk due to the condition are determined. Once trained, the machine-learnt classifier is instantiated as a matrix or matrices. The matrix maps the values of the input features to values of the result (e.g., condition). This mapping is used to predict the result in 28. For example, a condition of the patient, a risk for the patient, an outcome for treatment of the patient, a similar patient, or combinations thereof are predicted by the processor applying the values of the features to the machine trained classifier. The prediction or result may include probabilistic information, such as a probability or confidence score for the result or over a range of different possible results (e.g., 70% coronary obstruction, 25% problem with pulmonary arteries, and 5% aortic dissection).

As the machine-learnt model is used, the machine-learnt model may be updated. The results for a given patient are verified by a physician. The model being correct or not may be used to trigger whether to retrain the model. The verified results for a patient may be used as ground truth, providing another sample for training. The medical system may use any user-performed actions to improve the model performance, either in an online fashion or in an offline fashion. In the online case, the model automatically adapts the model parameters (e.g., weights in a neural network) as new information is acquired. Future predictions benefit from the knowledge gained during past patients or applications, not just those included in the training database. In the offline case, the user actions and additional information are stored for future processing. Once sufficient additional data is collected, the new data is combined with the existing data to train a new version of the machine-learnt model, which is then deployed in the clinical setting.

The machine-learnt model is hosted as a local application, for instance running directly on a medical scanner or a workstation connected to the patient information systems. Alternatively, the machine-learnt model is hosted as a service on a networked machine, such as a public or private cloud deployment with a server hosting the machine-learnt model. The output from the model may be a clinical report with key findings presented in a structured format for easy search and retrieval. Other outputs may be used, such as an alert, notification, filling in one or more fields in a patient medical record, or to a display.

There are various uses of the output of the determination. The result is output or recorded. The physician uses the output result to assist in diagnosis, treatment planning, or rendering advice to a patient. Acts 30-36 show four example uses. Other uses may be provided. Any combination of one or more uses of the results are used.

In act 30, the medical system provides a priority for triage based on the results. The results from multiple patients seeking emergency treatment are compared. For example, the results indicate risk over time or risk over time may be determined from the results (e.g., from a predicted condition). The patients may be ranked in order of risk so that the higher risk patients are treated more rapidly than lower risk patients.

In one embodiment, decision making under emergency conditions is guided by the results. In case of multiple patients requiring decision making in the emergency department, a trained machine-learnt classifier determines the order in which to see the patients and/or schedule examination. The machine-learnt classifier may also be used in combination with a constraint satisfaction problem (CSP) based approach to determine the schedule planning of the patients. CSP is used to optimize scheduling. To guide decision making under emergency conditions, the order in which to see the patients and/or the scheduling of exams in case of multiple patients requires decision making in the emergency department so as to obtain optimal outcome results for the patients. The machine learning algorithm may be employed to estimate the duration of each exam (based on prior exams of the patient, current symptoms, and/or similar patients from the past), whereas the CSP model may be used to then provide an optimal scheduling of these exams (taking into account several constraints, such as availability of devices and/or scanners, availability of clinicians, priority and/or urgency of examination, etc.). The input information available to the medical system for each patient seeking treatment includes data from prior examination of the patient (e.g., imaging, blood biomarkers, non-invasive measurements, demographic information, and the outcome), current symptoms, and the medical records of similar patients from the past (e.g., imaging, blood biomarkers, non-invasive measurements, demographic information and the outcome—specifically how crucial it was to obtain a fast diagnosis and/or treatment for these patients). The medical records of similar patients may not be available, but instead the machine-learnt classifier learns to relate such information to determine a schedule or priority for the current patients.

In other embodiments, the current patient data (ID, symptoms) may be provided by the patient in the ambulance and sent to the hospital while the patient is being brought to the hospital. In another variation, this data may be provided by the patient when the patient places the emergency call (providing symptoms during the emergency call). In yet another variation, the emergency call and triage may be triggered by a wearable (sensor) system, which performs continuous or regular monitoring and detects abnormal physiological parameters. The detection of abnormality may even be before the patient is aware that during the next minutes an emergency will exist.

The medical system may be based in the hospital or be a centralized system. The machine-learnt classifier accesses the data for the various patients and provides a scheduling solution in a rapid manner. Condition or other results may be provided to create the priority, or the priority itself may be the output result.

In another embodiment, the medical system is used in case of an insufficient number of ambulances so as to determine which patient to pick up first. A GPS-based system or any other system that estimates the travel times to the various patients and back to the hospital may be used to optimize the ambulance schedule in light of the risks to the patients. The medical system may determine, in case of patients located far away, if an ambulance or a faster transportation, like a helicopter, is required. The medical system may determine to which hospital the patient should be taken (e.g., depending on the available equipment, load of the hospital, distance from patient to hospital, and/or other information).

The determination of act 28 may be used to rank importance of missing values of features. Application of the machine-trained classifier to the extracted features with stochastic sampling of missing features is used to identify possible testing or actions to help make more accurate predictions and avoid testing or actions that are not likely to be determinative to the result.

In act 32, the medical system outputs a missing source of information based on the features that are available for the patient and the condition for the patient. Values may not be available for one or more features for the patient. Listing these features allows tests to be ordered or information to be gathered for that patient. Gathering missing information for all of the features may not be an optimum use of time, effort, money, or other resources. The results, such as predicted condition, from application of the machine-learnt classifier may be used to prioritize or select more determinative features. A stochastic distribution of values for the missing feature is used. The variation in predicted results over the distribution indicates the importance of the missing information, so is used to output a sub-set of one or more of the missing sources. The missing source more likely than other missing sources to result in prediction of a different condition, risk, or outcome is output as a recommendation for what data to gather (e.g., what test to perform).

Figure 5:
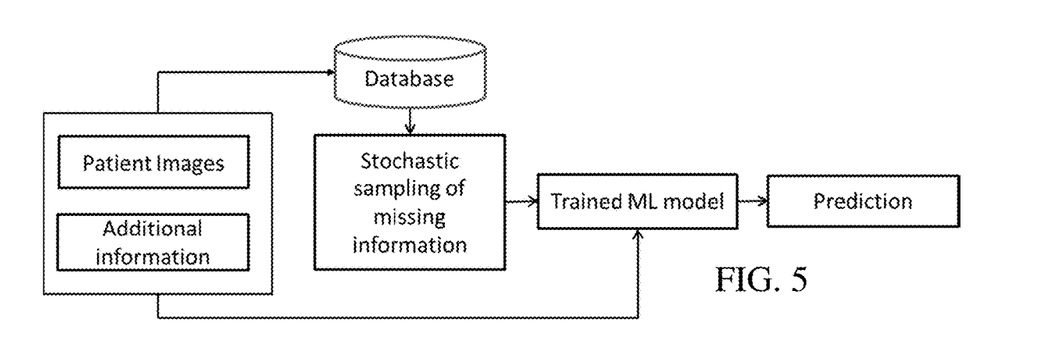
FIG. 5 illustrates populating input feature values with stochastic sampling to determine relevance of missing information.

FIG. 5 shows an example for how missing information is filled in using a database in a stochastic manner. The prediction is itself a stochastic output, reflecting the uncertainty in the unknown values. When new patient data is presented to the model, it is possible that some of the information sources are missing. In this case, the model uses database lookup based on the available information to find past cases close to the current patient information in the available features. Closeness may be measured with least square difference, vector dot product, binary matching, or other comparison of known values. The additional features from these past cases then provide a statistical distribution of the unknown features of the current patient. These missing parameters are then sampled according to this distribution stochastically to make multiple output predictions. This method results in not just a single prediction, but a distribution of predictions with a likelihood attached to each case. In this case, relatively low-likelihood, but high impact outcomes, for which additional testing should be prescribed are identified. These outcomes identify the patient-specific values of the missing pieces of information. If on the other hand, the distribution of the predicted outcomes is more narrow, then the additional features do not add much information, saving the patient from additional testing.

In act 34, the medical system provides decision support. Rather than just providing the predicted results, additional information is provided. For example, past cases for other patients similar to the current patient are identified. Similarity may be may be measured with least square difference, vector dot product, binary matching, or other comparison of known values. The search may be limited by the predicted results, such as limiting to patients with a same condition. Based on the identified cases of other patients, variation in treatment and outcome may be calculated. This distribution of treatments and outcomes is presented to guide decision making for treating the patient.

In another embodiment, a sub-set of data for a current patient is identified. A sub-set of the medical scan data, other data, or both is determined based on the output of the machine-learnt model or as the output of the machine-learnt model. For example, the machine-learnt model is trained to determine, based on current symptoms, the relevant past events of the patients that may help the clinician to take decisions faster. By selecting this sub-set of the data, a reduction of the consultation time, which is a critical aspect for clinicians, may result. By outputting the selected sub-set of data for review, the time that a clinician allocates to a single patient may be decreased.

In act 36, the machine-learnt classifier (recommender) is trained to recommend a wearable sensor. Alternatively, the medical system recommends a wearable sensor based on results output by the machine-learnt classifier. The input features and/or results are used to determine a wearable sensor appropriate for on-going or regular monitoring of the patient. For example, the predicted condition indicates that a given sensor should be prescribed. As another example, the sensor is recommended without specific identification of the condition. In either case, the measurements to be performed by a wearable system so as to ensure proper monitoring of the patient given the condition and past events are determined. A corresponding sensor is recommended to provide the measurements.

FIG. 6 shows a medical system for assisting in an emergency. The medical system includes a medical imaging system 11, a processor 13, a memory 15, and a display 16. The processor 13 and the memory 15 are shown separate from the medical imaging system 11, such associated with being a computer or workstation apart from the medical imaging system 11. In other embodiments, the processor 13 and/or memory 15 are part of the medical imaging system 11. In alternative embodiments, the medical system is a workstation, computer, or server. For example, the medical imaging system 11 is not provided or is provided for acquiring data representing a volume, and a separate database, server, workstation, and/or computer is provided for extracting features and applying a classifier to predict one or more results. Additional, different, or fewer components may be used.

The system is used for application of a machine-learnt model (e.g., one or more machine-learnt classifiers). In alternative embodiments, the system is used for training with machine learning and/or generation of the examples in the database.

The computing components, devices, or machines of the medical system, such as the medical imaging system 11 and/or the processor 13 are configured by hardware, software, and/or design to perform calculations or other acts. The computing components operate independently or in conjunction with each other to perform any given act, such as the acts of any of the methods described above. The act is performed by one of the computer components, another of the computing components, or a combination of the computing components. Other components may be used or controlled by the computing components to scan or perform other functions.

The medical imaging system 11 is any now known or later developed modality for scanning a patient. The medical imaging system 11 scans the patient. For example, a C-arm x-ray system (e.g., DynaCT from Siemens), CT like system, or CT system is used. Other modalities include MR, x-ray, angiography, fluoroscopy, PET, SPECT, or ultrasound. The medical imaging system 11 is configured to acquire the medical imaging data representing the patient. The data is acquired by scanning the patient using transmission by the scanner and/or by receiving signals from the patient.

The memory 15 is a buffer, cache, RAM, removable media, hard drive, magnetic, optical, database, or other now known or later developed memory. The memory 15 is a single device or group of two or more devices. The memory 15 is within the system 11, part of a computer with the processor 13, or is outside or remote from other components.

The memory 15 is configured to store medical scan data, other data, extracted features, examples (e.g., training data or data from other patients), and/or other information. Output results, information derived from the results, or calculations used to determine the results are stored in the memory 15. The memory 12 stores one or more matrices for the machine-learnt classifier or classifiers.

The memory 15 is additionally or alternatively a non-transitory computer readable storage medium with processing instructions. The memory 15 stores data representing instructions executable by the programmed processor 13. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 13 is a general processor, digital signal processor, three-dimensional data processor, graphics processing unit, application specific integrated circuit, field programmable gate array, digital circuit, analog circuit, combinations thereof, or other now known or later developed device for processing data. The processor 13 is a single device, a plurality of devices, or a network. For more than one device, parallel or sequential division of processing may be used. Different devices making up the processor 13 may perform different functions, such as extracting values for features by one device and applying a machine-learnt classifier by another device. In one embodiment, the processor 13 is a control processor or other processor of the medical imaging system 11. The processor 13 operates pursuant to stored instructions to perform various acts described herein.

The processor 13 is configured to extract values for features, to input the values, to output results, and/or to derive information from output results. The processor 13 applies the machine-learnt model to data for one or more patients. The condition, risk, outcome, identity of similar patients, and/or other information is determined by the processor 13 in an emergency setting.

The display 16 is a CRT, LCD, plasma, projector, printer, or other output device for showing an image. The display 16 displays the results or information derived from the results. Recommendations, missing sources (e.g., tests to be performed), triage prioritization, or other information is output to assist in diagnosis, treatment planning, and/or prognosis. Probabilities associated with any prediction, supporting data (e.g., values of input features), images from the medical scan data, and/or other information are output to assist the physician. By rapidly outputting the information due to the machine-learnt classifier's ability to deal with large amounts of data, emergency diagnosis and treatment is handled more efficiently, benefiting both the patients and the physicians.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for assessment and/or outcome determination in a medical system, the method comprising:
    acquiring medical scan data representing anatomical structures of patients being triaged in an emergency department of a hospital;
    obtaining other data for the patients;
    extracting a set of features from the medical scan data and the other data;
    inputting, by a processor, the features to a machine-trained classifier, the machine trained classifier trained, at least in part, from synthetically generated images not specific to training data for existing patient cases;
    determining, by the processor with application of the machine-trained classifier to the features, conditions of the patients and risks for the conditions;
    providing an order for triage of the patients based on the determined risks;
    identifying, by the processor, a missing source of information based on the features that are available for a first patient of the patients and the determined condition for the first patient, wherein the missing source of information is identified as more likely than other missing sources to result in a different condition or risk for the first patient; and
    outputting a recommendation to acquire the missing source of information.

2. The method of claim 1 wherein acquiring comprises acquiring computed tomography data of cardiac regions of the patients.

3. The method of claim 1 wherein obtaining other data comprises obtaining symptoms, patient demographics, blood biomarkers, patient history, non-invasive measurements, extracts from a clinical report, or combinations thereof.

4. The method of claim 1 wherein extracting the features from the medical scan data comprises applying a machine-learnt classifier to the medical scan data, the machine-learnt classifier and machine-trained classifier comprising a cascade.

5. The method of claim 1 wherein determining comprises determining with the application of the machine-trained classifier where the machine-trained classifier is trained from a forward model producing the synthetically generated images from variations in an anatomical model.

6. The method of claim 5 wherein the production of the synthetically generated images is guided by sampling of conditions of the training data.

7. The method of claim 1 wherein determining comprises determining with the application of the machine-trained classifier where the machine-trained classifier is trained from the synthetically generated images with different degrees of statistical noise added.

8. The method of claim 1 wherein acquiring comprises acquiring from a past scan of the first patient, and wherein obtaining comprises obtaining current symptoms.

9. The method of claim 1 wherein determining the risk for the first patient comprises determining with a dictionary of patient data with corresponding outcomes.

10. The method of claim 1 wherein inputting comprises inputting the features for the first patient and additional information extracted from other patients for missing features of the first patient, and wherein outputting comprises outputting the missing source based on a stochastic distribution resulting from the additional information.

11. The method of claim 1 further comprising identifying past cases similar to the first patient and indicating a distribution of treatments and outcomes.

12. The method of claim 1 further comprising identifying a sub-set of the medical scan data, other data, or both with a machine-learnt model and outputting the identified sub-set.

13. The method of claim 1 further comprising recommending a wearable sensor for the first patient based on a machine-learnt recommender applied to the other data, medical scan data, or both.

14. A method for assessment and/or outcome determination in a medical system, the method comprising:
   acquiring medical scan data representing anatomical structures of a patient in an emergency;
   obtaining other data for the patient;
   extracting a set of features from the medical scan data and the other data;
   determining, by the processor with application of the machine-trained classifier to the features, a condition of the patient, a risk for the patient, an outcome for the patient, a similar patient, or combinations thereof; and
   outputting a recommendation to acquire a missing source of information based on missing features for the patient and the determined condition, the determined risk, or the determined outcome of the patient, wherein the missing source is identified as more likely than other missing sources to result in a different condition, risk, or outcome for the patient.

15. The method of claim 14 wherein determining comprises determining with application of the machine-trained classifier to the extracted features and stochastic sampling of the missing features over additional information extracted from other patients, and
   wherein outputting comprises identifying the missing source based on results from the machine-trained classifier with the stochastic sampling.

16. The method of claim 14, further comprising:
   identifying, by the processor, the missing source of information based on missing features for the patient and the determined condition, the determined risk, or the determined outcome of the patient.

* * * * *